(12) United States Patent
Rolfe

(10) Patent No.: US 6,589,210 B1
(45) Date of Patent: Jul. 8, 2003

(54) INJECTION DEVICES

(75) Inventor: Steven Mark Guy Rolfe, Oxon (GB)

(73) Assignee: Owen Mumford Limited, Oxford (GB)

( * ) Notice: Subject to any disclaimer, the term of this patent is extended or adjusted under 35 U.S.C. 154(b) by 0 days.

(21) Appl. No.: 09/673,196

(22) PCT Filed: Feb. 15, 2000

(86) PCT No.: PCT/GB00/00482

§ 371 (c)(1),
(2), (4) Date: Oct. 12, 2000

(87) PCT Pub. No.: WO00/48655

PCT Pub. Date: Aug. 24, 2000

(30) Foreign Application Priority Data

Feb. 17, 1999 (GB) .............................................. 9903475

(51) Int. Cl.[7] .................................................. A61M 5/20

(52) U.S. Cl. ...................................... 604/157; 604/136

(58) Field of Search ................................ 604/181, 182, 604/187, 192, 197, 232, 218, 134, 135, 156, 157, 131; 128/919

(56) References Cited

U.S. PATENT DOCUMENTS

| | | | | |
|---|---|---|---|---|
| 3,880,163 A | | 4/1975 | Ritterskamp | |
| 5,085,642 A | * | 2/1992 | Sarnoff et al. | 604/134 |
| 5,092,842 A | * | 3/1992 | Bechtold et al. | 604/135 |
| 5,122,119 A | | 6/1992 | Lucas | |
| 5,593,388 A | * | 1/1997 | Phillips | 604/131 |
| 5,779,677 A | * | 7/1998 | Frezza | 604/131 |
| 6,159,181 A | * | 12/2000 | Crossman et al. | 604/134 |
| 6,270,479 B1 | * | 8/2001 | Bergens et al. | 604/156 |

FOREIGN PATENT DOCUMENTS

WO    WO 99/03529    1/1999

* cited by examiner

Primary Examiner—Brian L. Casler
Assistant Examiner—Mark K. Han
(74) Attorney, Agent, or Firm—Young & Thompson

(57) ABSTRACT

An injection device houses a syringe and contains a drive spring, to urge the syringe forwards to project its needle and then eject the dose, and a return spring, to push the syringe back into the housing and retract the needle. A trigger is operated in one way to release the drive spring and in another way to release the return spring, these operations being mutually exclusive and there being parts for ensuring they are performed in the correct order.

10 Claims, 2 Drawing Sheets

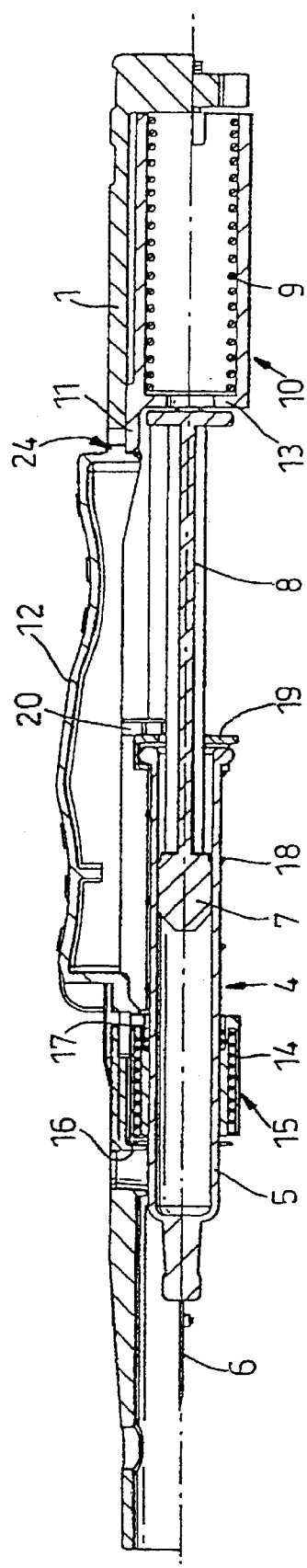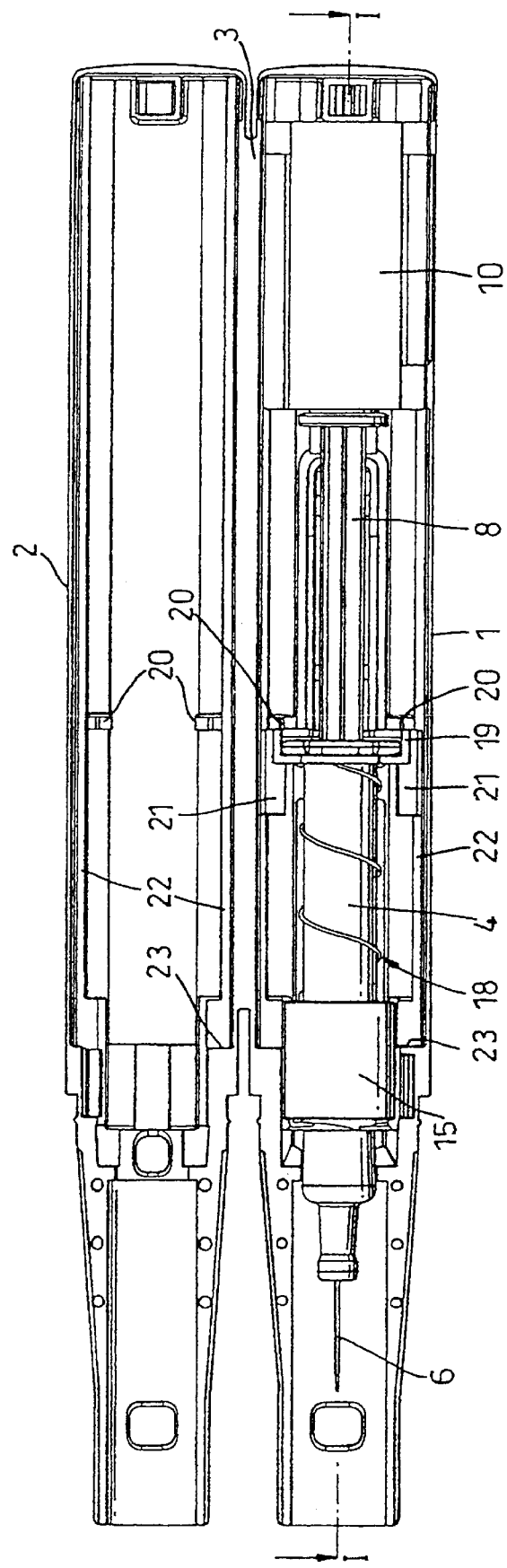

INJECTION DEVICES

BACKGROUND OF THE INVENTION

This invention relates to injection devices.

It concerns devices which are fitted with a syringe having a capsule with a needle projecting from the forward end and a plunger from the rear end. A trigger and spring mechanism, when operated, shoots the syringe forwardly to project the needle, and then continues to act on the plunger to eject the dose. There is also a return spring arrangement to retract the needle after use, thereby making it safe.

DESCRIPTION OF THE RELATED ART

In WO 99/03529 we have described such a device in which the trigger is arranges to provide an obstruction to the syringe, after its needle has been projected to prevent the syringe being retracted until the trigger is released or operated in another manner. Then the return spring can act.

This works well enough, but there is a potential problem with the device if it is used with a syringe with a low volume of prefill. The total movement of the plunger can then be insufficient to allow the differential between the drive and return springs to permit the syringe to retract satisfactorily.

SUMMARY OF THE INVENTION

It is the aim of this invention to ensure a more certain retraction.

According to the present invention there is provided an injection device for containing and operating a syringe having a capsule with a needle projecting from the forward end and a plunger from the rear end, the device having a barrel enclosing the syringe and first and second springs initially held by a trigger assembly carried by the barrel in compressed energised states respectively at the rear and towards the forward ends of the barrel, wherein a first operation of the trigger assembly releases the first spring but keeps the second spring compressed so that the first spring urges the syringe forwardly by acting on the plunger and thence through the dose within the syringe, and then, when the syringe reaches a needle projecting position, presses the plunger forwards relative to the capsule to eject the dose, and wherein a second, different operation of the trigger assembly releases the second spring which exerts itself to retract the syringe and its needle.

Preferably means will be provided for preventing the second operation of the trigger assembly before the first operation.

The first, drive spring is conveniently housed in a cylindrical slider and acts between the rear end of the barrel and the forward end of the slider.

Preferably the second, return spring is housed in a cylindrical carrier surrounding the capsule and acts between the rear end of the carrier and an abutment forward of the carrier provided by the barrel. This can locate in the barrel and provide a guide for the syringe as well as containment for the return spring.

The trigger assembly is conveniently a single rocker aligned longitudinally of the barrel, its rear end co-operating with the slider, to release that when its forward end is pressed in as said first operation, and its forward end co-operating with the carrier, to release that when its rear end is pressed in as said second operation. The co-operation of the rear end of the rocker with the slider can be the agency preventing that rear end being pressed in until after the slider has moved the syringe to its needle projecting position.

Since the return spring is out of commission until the injection has been carried out, a third, light spring may be provided to keep the syringe retracted against a stop until the device is fired. This will present no significant resistance to the main drive spring when that is released.

This containment of the return spring until it is actually needed means that it can be powerful enough to ensure retraction whatever the prefill and the amount the main drive spring hogan expanded.

BRIEF DESCRIPTION OF THE DRAWINGS

For a better understanding of the invention one embodiment will now be described, by way of example, with reference to the accompanying drawings, in which:

FIG. 1 is a part axial section of an injection device, the section being on line I—I of FIG. 2.

FIG. 2 is a plan view of the device in a folded out condition before assembly is complete.

DESCRIPTION OF THE PREFERRED EMBODIMENTS

Figure 3:
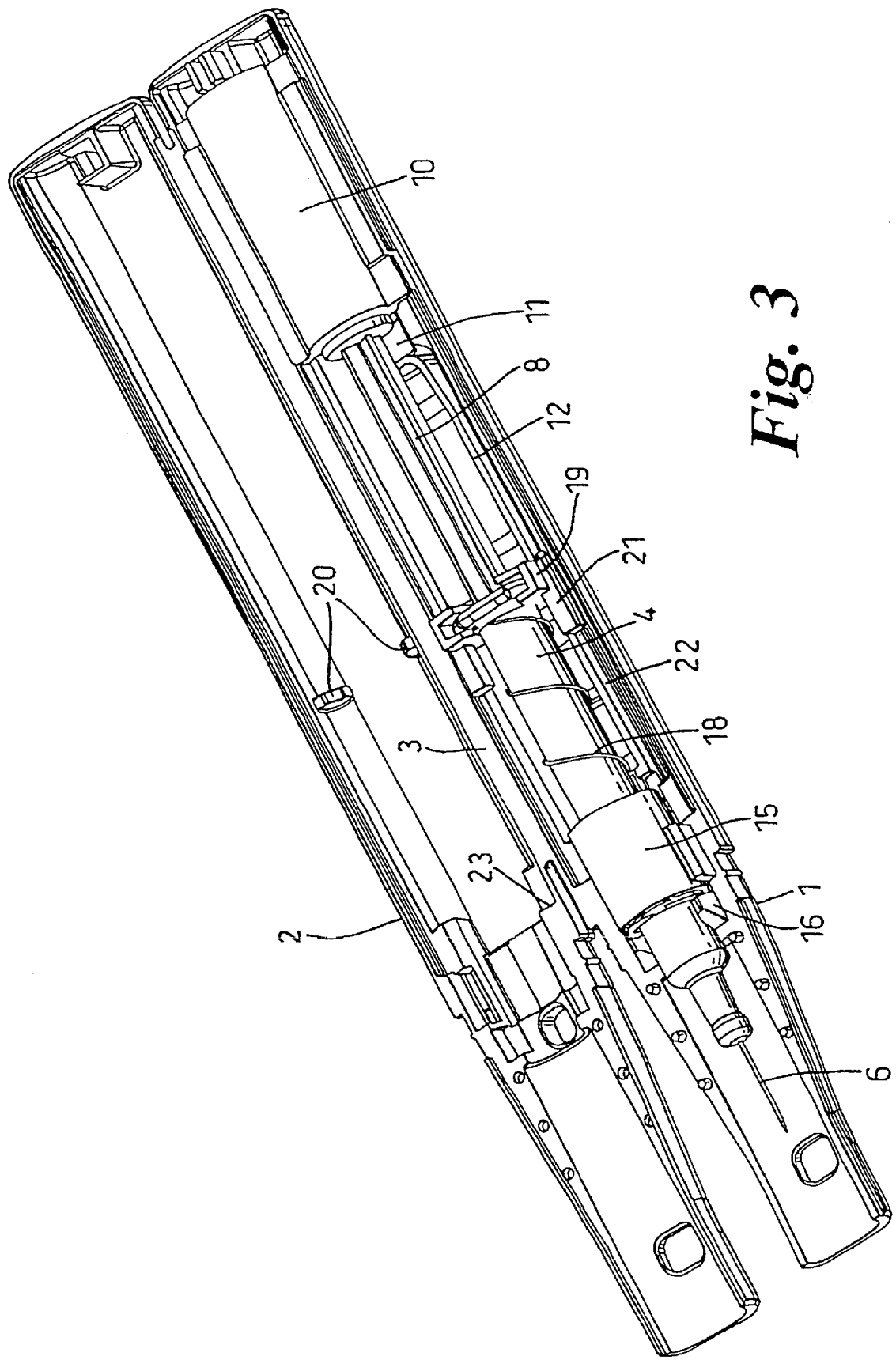
FIG. 3 is a perspective view of the device in the condition of FIG. 2.

The injection device has a barrel integrally moulded in two halves 1 and 2 connected by a thin web 3 which serves as a hinge to allow the halves to be closed together when the interior components have been assembled.

The device is for housing and operating a syringe 4 comprising a capsule 5, a needle 6 projecting from its leading end, a piston 7 confining the dose, and a piston rod 8 projecting from the rear end of the capsule. The device projects the needle 6 by spring action on the piston rod 8, which acts through the dose in the syringe, and then ejects the dose by continuance of that spring action. Finally it retracts the syringe by means of a further spring.

The main drive spring 9 is housed in a cylindrical slider 10 at the rear end of the barrel, the slider having a tongue 11 that is initially engaged by the rear end of a trigger 12. This is integrally formed with the barrel and is of the rocker type. In its normal, initial position it keeps the spring 9 fully compressed between the closed rear end of the barrel and an inturned flange 13 at the leading end of the slider 10 The syringe is initially positioned so that the rear end of its piston rod 8 is immediately in front of the flange 13 of the slider 10 when that syringe has a full dose. For lesser prefills, there will be a gap between the rod 8 and slider 10.

A return spring 14 is pre-compressed and held in its own carrier 15. This is cylindrical and double walled to provide an annular space for the spring 14, open at the forward end and closed at the rear end. It locates snugly within the barrel with the forward end of the spring 14 against a shoulder 16 provided by the barrel and the rear end of the carrier 15 initially engaged by the forward end of the trigger 12, this holding the spring 14 compressed. The carrier 15 also provides a guide for the syringe 4, around which it forms a collar.

At its rear end, the carrier 15 has an interior annular rebate 17 to locate the forward end of a third spring 18 which coils with coarse pitch around the syringe 4 back to an abutment 19 which fits the outwardly beaded rear end of the syringe. The bead itself is not prominent enough, and the abutment 19, which slots over it laterally, effectively enlarges it. The abutment 19 also co-operates with lugs 20 on the inside of the barrel halves 1 and 2 which limit rearward movement Sliders 21 integral with the abutment 19 are guided longitudinally, of the barrel in grooves 22 completed when the halves 1 and 2 are closed together. The forward ends 23 of these grooves serve as stops.

As explained below, the trigger 12 is operated twice, in two different ways, and to ensure that this is done in the correct sequence the rear end of the trigger has a small lug 24 projecting back over the forward end of the tongue 11. This prevents the rear end of the trigger 12 being pressed in when the device is in its initial, primed position as shown in FIG. 1.

For use of the device, starting from that position, the forward end of the trigger 12 is pressed, lifting the rear end clear of the tongue 11. The drive spring 9 is therefore released and shoots the slider 10 forwards, and with it the piston rod 8 and piston 7. The dose, incapable of rapid escape, acts as a solid in known manner, and so the syringe 4 is carried forwards projecting the needle 6 from the barrel. The weak spring 18, which serves only to keep the syringe retracted before firing, offers negligible resistance and is easily compressed. The trigger 12 keeps its engagement with the return spring carrier 15 at this point and the spring 14 therefore offers no resistance.

The syringe is arrested by the sliders 21 coming up against the stops 23. The spring 9 continues to expand and, through the slider 10 and piston rod 8, ejects the dose through the needle 6.

The trigger 12 is then released. The slider 10, having travelled beyond the rear end of the trigger, does not provide any obstruction to the resumption of its initial position. The trigger can then be pressed in at the rear end, bringing its forward end outwards and clear of the carrier 15. The return spring 14 is therefore released and, through the abutment 19, which has been closed up almost to the carrier 15, it urges the syringe back into the barrel, retracting the needle Since this spring 14 is kept compressed until this stage and does not have to be energised by the drive spring, it can easily be powerful enough to overcome the extended drive spring and push the syringe back.

The syringe is thus spent and the device safe.

The trigger 12 in its rocker form is preferred for simplicity. However, its two functions could be performed by two separate triggers, although to ensure that they are operated in the correct sequence the one that releases the return spring would have to be incapacitated until after the device has been fired, requiring a more complicated interlock system than the lug 24 and the tongue 11.

What is claimed is:

1. An injection device for containing and operating a syringe having a capsule with a needle projecting from the forward end of the syringe and a plunger from a rear end of the syringe, the device comprising:

a barrel enclosing the syringe and a first, drive spring and a second return spring initially held by a trigger assembly carried by the barrel in compressed energised states at a rear end of the barrel and towards a forward end of the barrel respectively, wherein
   a first operation of the trigger assembly releases the first, drive spring but keeps the second, return spring compressed so that the first spring urges the syringe forwardly by acting on the plunger and thence through the dose within the syringe, and then, when the syringe reaches a needle projecting position, presses the plunger forwards relative to the capsule to eject the dose, a second, different operation of the trigger assembly releases the second, return spring which exerts itself to retract the syringe and its needle, and said trigger assembly is manually operable to perform said second operation independently of said first operation.

2. An injection device as claimed in claim 1, wherein means are provided for preventing the second operation of the trigger assembly before the first operation.

3. An injection device as claimed in claim 2, wherein the second return spring is housed in a cylindrical carrier surrounding the capsule and acts between the rear end of the carrier and an abutment forward of the carrier provided by the barrel.

4. An injection device as claimed in claim 3, wherein the carrier locates in the barrel and provides a guide for the syringe as well as containment for the return spring.

5. An injection device as claimed in claim 4, wherein the co-operation of the rear end of the rocker with the slider prevents that rear end being pressed in until after the slider has moved the syringe to its needle projecting position.

6. An injection device as claimed in claim 3, wherein the first, drive spring is housed in a cylindrical slider and acts between the rear end of the barrel and a forward end of the slider, and wherein the trigger assembly is a single rocker aligned longitudinally of the barrel, said rocker having a rear end co-operating with the slider, to release that when the forward end of said rocker is pressed in as said first operation, and said rocker having a forward end co-operating with the carrier, to release the carrier when the rear end of said rocker is pressed in as said second operation.

7. An injection device as claimed in claim 1, wherein the first, drive spring is housed in a cylindrical slider and acts between the rear end of the barrel and the forward end of the slider.

8. An injection device as claimed in claim 1, wherein a third spring is provided to keep the syringe retracted against a stop until the device is fired, the third spring presenting no significant resistance to the main drive spring when that is released.

9. An injection device as claimed in claim 1, wherein the second return spring is housed in a cylindrical carrier surrounding the capsule and acts between the rear end of the carrier and an abutment forward of the carrier provided by the barrel.

10. An injection device for containing and operating a syringe having a capsule with a needle projecting from a forward end of the syringe and a plunger from a rear end of the syringe, the device comprising:

a barrel enclosing the syringe and a first, drive spring and a second, return spring initially held by a trigger assembly carried by the barrel in compressed energised states at a rear end of the barrel and towards a forward end of the barrel respectively, said trigger assembly comprising a trigger element having a first detent region for maintaining said first, drive spring in its compressed energised state, and a second detent region for maintaining said second, return spring in its compressed energised state, wherein
    a first operation of the trigger assembly releases the first, drive spring but keeps the second, return spring compressed so that the first, drive spring urges the syringe forwardly by acting on the plunger and thence through the dose within the syringe, and then, when the syringe reaches a needle projecting position, presses the plunger forwards relative to the capsule to eject the dose, a second, different operation of the trigger assembly releases the second, return spring which exerts itself to retract the syringe and its needle, and said trigger assembly is manually operable to perform said second operation independently of said first operation.

* * * * *